(12) United States Patent
Fox

(10) Patent No.: US 7,122,065 B2
(45) Date of Patent: Oct. 17, 2006

(54) ADAPTER FOR LOW VOLUME AIR SAMPLER

(75) Inventor: Richard B. Fox, Mesa, AZ (US)

(73) Assignee: Honeywell International, Inc., Morristown, NJ (US)

( * ) Notice: Subject to any disclaimer, the term of this patent is extended or adjusted under 35 U.S.C. 154(b) by 287 days.

(21) Appl. No.: 10/788,090

(22) Filed: Feb. 25, 2004

(65) Prior Publication Data

US 2005/0183575 A1    Aug. 25, 2005

(51) Int. Cl.
*B01J 20/26* (2006.01)
*G01N 30/96* (2006.01)

(52) U.S. Cl. .................. 55/306; 55/439; 55/422; 55/385.1; 55/385.4; 95/133; 95/286; 95/287; 96/413; 96/108; 73/28.01; 73/31.02; 73/863.22; 73/863.23; 422/88; 422/101

(58) Field of Classification Search ............ 55/306, 55/439, 385.1, 385.4, 422; 95/287, 133, 95/286; 96/413, 108; 73/863.22, 863.23, 73/28.01, 31.02; 422/88, 101
See application file for complete search history.

(56) References Cited

U.S. PATENT DOCUMENTS

| 868,931 | A |  | 10/1907 | Kuszmaul, Jr. |
| 2,083,035 | A |  | 6/1937 | Rogers |
| 2,103,838 | A |  | 12/1937 | Bach |
| 2,230,098 | A |  | 1/1941 | Wurzburger |
| 3,059,470 | A | * | 10/1962 | Baldwin et al. ......... 73/863.23 |
| 3,593,023 | A |  | 7/1971 | Fullerton et al. |
| 3,866,474 | A |  | 2/1975 | Hasselmann |
| 3,866,950 | A |  | 2/1975 | Skoch et al. |
| 3,870,492 | A |  | 3/1975 | Guild |
| 4,137,647 | A |  | 2/1979 | Clark, Jr. |
| 4,170,901 | A |  | 10/1979 | Conkle et al. |
| 4,304,578 | A | * | 12/1981 | Hakala et al. ............ 55/439 |
| 4,612,019 | A |  | 9/1986 | Langhorst |
| 4,632,019 | A |  | 12/1986 | Whiteman |
| 4,756,200 | A |  | 7/1988 | Ramsner et al. |
| 4,863,202 | A |  | 9/1989 | Oldford |
| 4,893,848 | A |  | 1/1990 | Melcher |
| 4,902,318 | A | * | 2/1990 | Stevens et al. ......... 73/863.22 |
| 5,125,277 | A | * | 6/1992 | Zievers .................. 73/863.23 |
| 5,553,895 | A |  | 9/1996 | Karl et al. |
| 5,621,180 | A |  | 4/1997 | Simon et al. |

(Continued)

FOREIGN PATENT DOCUMENTS

WO    PCT/2005/008098    6/2005

*Primary Examiner*—Duane Smith
*Assistant Examiner*—Minh-Chau T. Pham
(74) *Attorney, Agent, or Firm*—Ingrassia Fisher & Lorenz

(57) ABSTRACT

An adapter for use with a low volume PUF sampler is described. The adapter is affixed over the open end of a PUF (polyurethane foam) sample cartridge. Sample tubing is affixed to an aperture in the adapter, and the free end of the sample tubing is then positioned at a desired sample location such as within an aircraft interior. As a vacuum is applied to the PUF cartridge, the adapter allows air collected at the sample point to pass through the tubing and through the interior of the PUF cartridge while preventing air surrounding the PUF cartridge from being drawn into the PUF cartridge except through the sample tubing. In this manner the sample point of a desired air sample can be selected at a point remote from the PUF cartridge. Additionally, use of multiple PUF cartridges and adapters allows the simultaneous collection of separate air samples.

7 Claims, 3 Drawing Sheets

U.S. PATENT DOCUMENTS

| | | |
|---|---|---|
| 5,637,792 A | 6/1997 | Kimura et al. |
| 5,702,506 A * | 12/1997 | Shih et al. .................... 95/287 |
| 5,750,999 A | 5/1998 | Fox |
| 5,763,360 A * | 6/1998 | Gundel et al. .............. 502/402 |
| 5,765,612 A | 6/1998 | Morin |
| 5,794,986 A | 8/1998 | Gansel et al. |
| 5,800,597 A * | 9/1998 | Perrotta et al. .................. 96/9 |
| 5,907,109 A | 5/1999 | Tedeschi |
| 5,921,592 A | 7/1999 | Donnelly |
| 6,087,183 A * | 7/2000 | Zaromb ..................... 436/178 |
| 6,138,521 A | 10/2000 | Basch et al. |
| 6,217,441 B1 | 4/2001 | Pearman et al. |
| 6,226,852 B1 | 5/2001 | Gundel et al. |
| 6,244,117 B1 | 6/2001 | Mengel et al. |
| 6,418,801 B1 | 7/2002 | Lewis |
| 6,471,582 B1 | 10/2002 | Tucker |
| 6,477,906 B1 | 11/2002 | Peterson |
| 6,517,593 B1 * | 2/2003 | Robertson et al. ......... 55/385.1 |
| 6,632,271 B1 * | 10/2003 | Robertson et al. ............ 96/413 |
| 6,743,278 B1 * | 6/2004 | Carruthers .................... 95/133 |
| 6,761,757 B1 * | 7/2004 | Welker ........................ 96/413 |
| 2001/0045000 A1 | 11/2001 | Gundel et al. |
| 2002/0071786 A1 | 6/2002 | Schneiber, Jr. et al. |
| 2002/0153725 A1 | 10/2002 | Myers |
| 2002/0189332 A1 | 12/2002 | Schell |
| 2003/0008341 A1 | 1/2003 | Spurrell |
| 2003/0012696 A1 | 1/2003 | Millancourt |

* cited by examiner

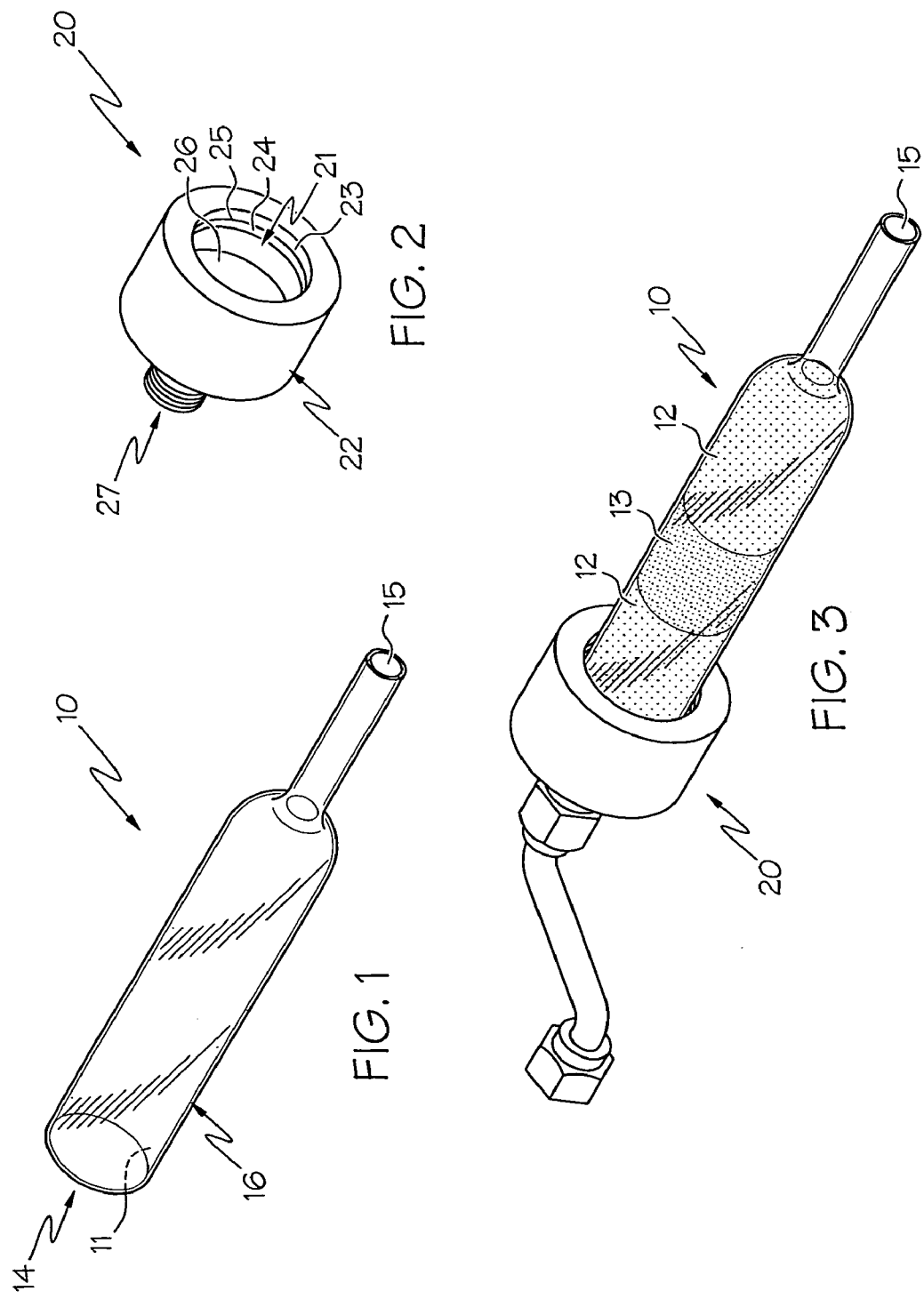

ADAPTER FOR LOW VOLUME AIR SAMPLER

This application is related to U.S. patent application Ser. No. [not yet assigned] entitled "High Volume Air Sampler."

FIELD OF THE INVENTION

The present invention relates to low volume air sampling. More particularly the invention relates to methods and equipment used for taking air samples from an enclosed volume such as that encountered in an aircraft cabin. In particular the present invention also relates to use of a low volume air sampling PUF cartridge, adapters, and associated ductwork.

BACKGROUND OF THE INVENTION

Air samplers are finding increased application in a variety of uses. One such application deals with the transportation industry. For example, passengers may be subject to noxious smells or gases or other airborne impurities when traveling in enclosed vehicles such as trains, motor coaches, or airplanes.

When an event occurs during which passengers are subject to odors, smoke, gases, or other undesirable airborne impurities, it is desirable to perform some kind of test or sampling. The testing or sampling of the air supply may be done for several reasons. It may be desired to repeat the incident of impure air flow in order to sample the air and thus trace the source of impurity. Additionally, the testing or sampling may be performed in part to certify that, once corrected, the vehicle in question is again supplying clean air to passengers.

In the example of a modern passenger jetliner, air supply to the interior cabin often begins with the gas turbine engines. In the typical structure of a gas turbine engine, including those used in industrial, marine, vehicle, as well as aerojet applications, air enters the engine inlet and first passes through a series of compressor stages such as a low pressure stage and a high pressure stage. The air then passes through a combustion chamber and, in exiting the engine, crosses turbines such as high pressure and low pressure turbines. However, a significant portion of air that enters the engine inlet passes around the compressors, combustion chamber and turbines, this is called fan air. Additionally air in the compressors may be bled off for deicing and other pneumatic applications through bleed valves. Bleed valves are typically used to select air at a desired pressure within the gas turbine engine. Environmental control systems used in commercial airliners often draw air from either ram or the bleed valves. This air may then pass through ductwork, pumps, temperature controls, and other air handling equipment before being vented into the passenger cabin. In some applications, air may be extracted from a compressor which is not an integral part of an engine.

Present in these turbine propulsion engines as well as the APU's (auxiliary power units) are fluid sealing systems. Sealing systems typically work to contain materials such as lubricants and hydrocarbons within the engine body. For example sealing systems are employed within a gas turbine engine to prevent trace elements of materials such as fuel or lubricant from leaking from the engine and into the bleed air. However, such sealing systems are not always totally effective, and as a result there may be leakage of fuel or lubricant into the bleed air. Hence hydrocarbons and lubricants within the engine may often be a source of semivolatile compounds that result in odors and noxious impurities that are harmful or unpleasant to the passengers. Hydrocarbons for example can oxidize and produce smoke in the air flowing into the cabin.

Previous methods used to measure contaminants in engine bleed air have either been inconclusive or have given false readings. One such method incorporates a polyvinylchloride filter to collect a sample of the bleed air followed by looking for the presence of oil by using a black light to make the oil droplets fluoresce. Another method includes the use of a large, stainless steel coil chilled to about $-100$ degrees F. to condense matter in the bleed air. The condensed matter is then flushed from the coil, evaporated with a solvent (freon) and weighed. In a third method, the bleed air is flowed through absorption tubes in which residue is collected on silica gel, charcoal, or molecular sieves and then evaluated by gas chromatography/mass spectroscopy. The residue can also be analyzed by combusting its organic matter, and measuring the carbon dioxide formed with a flame ionization detector or nitrogen phosphorous detector.

Presently, there is no known equipment available that is designed to sample high volumes of air from a closed system. In particular there is no known equipment designed to take high volume air samples from the supply system of a closed aircraft fuselage. Accordingly there is a need for a high volume air sampler that can screen for particulate, volatile, and semivolatile materials present in the air sample.

In a closed environment, such as the fuselage interior of a commercial jet airplane, traditional methods of taking air samples face difficulties. In the typical known method for taking air samples a collector is exposed to the environment where it is desired to take an air sample. One end of the collector is open to the atmosphere and an opposite end of the collector is attached to a pump (typically with an intervening hose). Running the pump pulls a vacuum which serves to pull air through the collector.

The difficulty of such an arrangement in a closed environment is that current equipment is not designed to be used in a closed ducted system. Thus it is difficult to take air samples with this arrangement. However, low volume air samples are sometimes preferred when restricted power may require utilizing a battery power or similar low power vacuum pump. In such a case it is often necessary to sample a large volume of air over an extended period of time in order to capture a sufficient quantity of the contaminant in order to subject the impurity to analysis.

Low volume PUF samplers have also been used to capture semivolatile compounds in ambient air. As used in testing the air in an aircraft for airborne impurities, a low volume PUF sampler has a typical measuring sensitivity in the range of parts per million to high parts per billion, while being able to operate with a battery powered pump.

Recently it has been desired to collect air samples from specific locations within an aircraft body. However, no adapter has ever been invented which allows the capture of semivolatile organic compounds from remote locations utilizing the low volume PUF samplers. In the airline industry there is a need for an apparatus and method to take low volume air samples that may include semivolatile compounds. In particular, there is a need for an adapter that would allow sampling of semivolatile compounds using known sampling equipment such as a PUF sampler.

While apparatuses and methods of sampling semivolatile organic compounds are known; nevertheless, there is a need for an improved apparatus and method that overcomes one or more of the above-noted drawbacks. Namely, an apparatus is needed that will allow low volume sampling of semivolatile compounds in an enclosed environment such as the interior of an aircraft Further it is desired that the sampling method be able to collect air samples from specific locations with the airplane. It is also desired to collect samples from different locations within an airplane simultaneously. The PUF cartridge adapter disclosed herein addresses one of more of these needs.

SUMMARY OF THE INVENTION

The present invention provides a collector adapter and method for using the same. The adapter allows for the collection of an air sample including sampling semivolatile organic compounds in an air sample as for example may be found in the interior space of an aircraft. The adapter is particularly suited for use with PUF sample casings or housings.

In one embodiment and by way of example only there is provided an adapter for use with a PUF cartridge comprising: a body having an interior surface and an exterior surface; said body further defining an aperture allowing fluid communication therethrough; and a sealing surface located on said interior surface of said body. The adapter may further comprise a fitting and/or a fitting attached to the adapter with interlocking threads. The sealing surface may further include a gasket and/or a washer positioned within a groove on the interior surface of the body. The body may be cylindrical in shape.

In a further embodiment and by way of example only there is provided an apparatus for taking an air sample from the interior of an aircraft body comprising: a PUF cartridge defining an interior and an exterior; said PUF cartridge further having an opening and an exit; an adapter affixed to said PUF cartridge over said opening; a vacuum source; tubing having two ends connected at one end to said vacuum source and at the other end to said exit of said PUF cartridge; and sample tubing having two ends with one end positioned at a sample location and the other end affixed to said adapter. The adapter may sealingly engage with the PUF cartridge. The adapter may further define an interior surface with a groove and further comprise a washer positioned within said groove and configured to seal against said exterior of said PUF cartridge. The adapter may also include a stop. The PUF cartridge may comprise adsorbent resin disposed within the interior of the PUF cartridge. Additionally the PUF cartridge may further include polyurethane foam disposed within the interior of the PUF cartridge. Further the apparatus may further define an aperture which includes a fitting for receiving sample tubing, with the fitting positioned within the aperture whereby the aperture and fitting provide fluid communication from the exterior of the PUF cartridge to the interior of the PUF cartridge.

In still a further embodiment and still by example only there is provided an apparatus for sampling air from multiple sample points comprising: a first PUF cartridge defining an interior and an exterior; said first PUF cartridge further having an opening and an exit; a second PUF cartridge defining an interior and an exterior; said second PUF cartridge further having an opening and an exit; a first adapter affixed to said first PUF cartridge over said opening; a second adapter affixed to said second PUF cartridge over said opening; a vacuum source; a first tubing having two ends connected at one end to said vacuum source and at the other end to said exit of said first PUF cartridge; a second tubing having two ends connected at one end to said vacuum source and at the other end to said exit of said second PUF cartridge; a first sample tubing having two ends with one end positioned at a first sample location and the other end affixed to said first adapter; and a second sample tubing having two ends with one end positioned at a second sample location, remote from said first sample location, and the other end affixed to said second adapter. Additionally the first adapter may further define an aperture and said first adapter further comprise a fitting for receiving said first sample tubing, said fitting positioned within said aperture whereby said aperture and said fitting provide fluid communication from the exterior of said first PUF cartridge to the interior of said first PUF cartridge; and wherein said second adapter may further define an aperture and said second adapter may further comprise a fitting for receiving said second sample tubing, said fitting positioned within said aperture whereby said aperture and said fitting provide fluid communication from the exterior of said second PUF cartridge to the interior of said second PUF cartridge.

In still a further embodiment also by way of example only there is provided a method for detecting semivolatile compounds in an air sample comprising: loading a PUF cartridge with an adsorbent compound; affixing an adapter over the opening of a PUF cartridge; positioning sample tubing at a sample point; and drawing a vacuum at the exit of said PUF cartridge. This method may further comprise loading polyurethane foam in the PUF cartridge and affixing sample tubing to an adapter aperture. Further the step of affixing the adapter over the opening of a PUF cartridge may further comprise sliding the adapter over the opening until the PUF cartridge contacts a stop on said adapter. The step of affixing the adapter over the opening of a PUF cartridge may further comprise placing a sealing ring in sealing contact against the exterior surface of the PUF cartridge. The method may further include analyzing the adsorbent compound for the presence semivolatile compounds.

In still an additional exemplary embodiment there is provided a method for sampling semivolatile compounds from multiple sample points comprising the steps of: providing a first PUF cartridge loaded with a first selected adsorbent compound; providing a second PUF cartridge loaded with a selected adsorbent compound; sealingly attaching a first adapter over the opening of said first PUF cartridge; sealingly attaching a second adapter over the opening of said second PUF cartridge; attaching said first PUF cartridge and said second PUF cartridge to a vacuum source; positioning a first sample tubing at a first sample point; positioning a second sample tubing at a second sample point; and pulling a vacuum through said first PUF cartridge and through said second PUF cartridge until a desired volume of air has passed through said first and said second PUF cartridges; retrieving said adsorbent compound from said first PUF cartridge and said second PUF cartridge; and analyzing said adsorbent compound for the presence of semivolatile compounds.

Other independent features and advantages of the low volume PUF sampler system will become apparent from the following detailed description, taken in conjunction with the accompanying drawings which illustrate, by way of example, the principles of the invention.

BRIEF DESCRIPTION OF THE DRAWINGS

FIG. 1 is an illustration of the PUF cartridge used in accordance with an embodiment of the invention.

FIG. 2 is an illustration of the PUF sampler adapter in accordance with an embodiment of the invention.

FIG. 3 is an illustration of the PUF sampler adapter affixed to a PUF cartridge according to an embodiment of the invention.

DETAILED DESCRIPTION OF A PREFERRED EMBODIMENT

Figure 4:
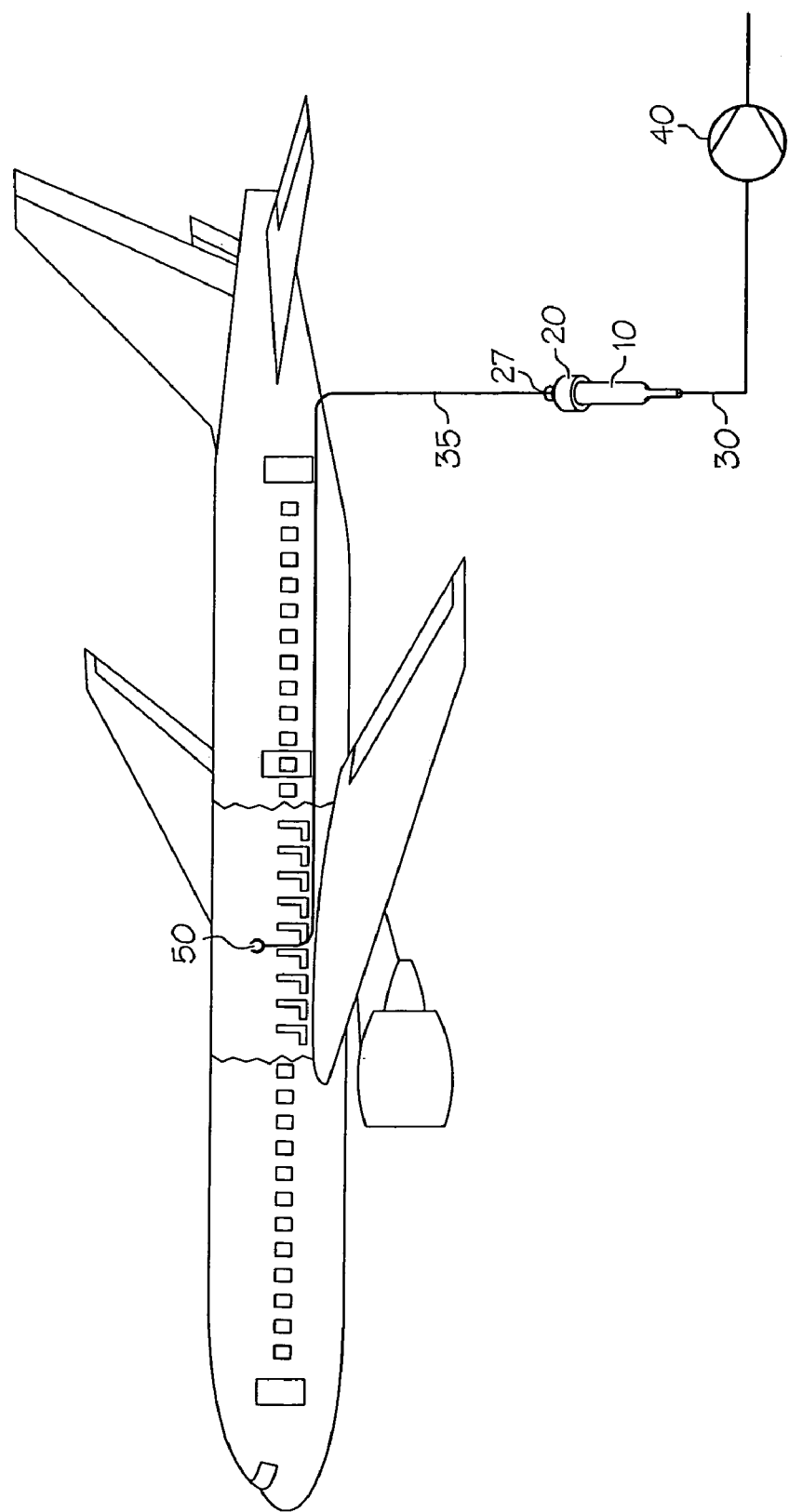
FIG. 4 is an illustration of an air sampling system using the low volume sample adapter in accordance with an embodiment of the invention.

Reference will now be made in detail to exemplary embodiments of the invention, examples of which are illustrated in the accompanying drawings. Wherever possible, the same reference numbers will be used throughout the drawings to refer to the same or like parts.

In one preferred embodiment, the present system is designed for use with known sampling housings such as a PUF cartridge. PUF is a general acronym for Polyurethane Foam, a material used for sampling airborne materials and contaminants such as semivolatile compounds. The Killdee Scientific Glass Company is one such manufacturer of the PUF cartridge.

As shown in FIG. 1 the PUF cartridge 10 is a generally hollow vessel defining an interior region 11 and exterior region 16. The PUF cartridge is typically manufactured of glass, however other materials such as metals, alloys, and plastics may also be used. In its operational configuration, shown in FIG. 3, the PUF cartridge 10 typically includes a foam packing 12, an adsorbent resin 13, and additional foam packing 12. Referring again to FIG. 1, the cartridge itself includes opening 14 and exit 15. In a preferred usage, adsorbent resin 13 is sandwiched between layers of foam packing 12 thereby holding the adsorbent resin in place. Also as shown in FIG. 1 the PUF cartridge 10 has an opening 14 that is exposed to the atmosphere.

In known applications of the PUF cartridge 10 a tubing 30 or line is attached to exit 15. This tubing or line is itself attached to a vacuum source such as a vacuum pump 40. When a vacuum is drawn by the vacuum pump 40, air will then be sucked through opening 14 through the interior of the PUF cartridge 11 across foam packing 12 and adsorbent resin 13 and then through exit 15. As the air sample is drawn through the PUF cartridge, airborne contaminants such as semivolatile compounds are thereby carried through the PUF cartridge. Upon encountering adsorbent resin 13, semivolatile compounds react with adsorbent resin 13. In a preferred method, semivolatile compounds react with adsorbent resin 13 by adhering to adsorbent resin 13. In this manner, upon drawing a sufficient volume of air across the PUF cartridge, the adsorbent resin 13 can be removed from the interior 11 of the PUF cartridge and analyzed. Analysis of the adsorbent resin will reveal the composition of the semivolatile compounds present in the air sample. Additionally, knowledge of the air volume that passed through the PUF sampler will thereby indicate the concentrations of the semivolatile compounds in the air sample.

As is known in the art, an adsorbent resin 13 may be selected for its reactivity to certain known or targeted contaminants. Thus, different materials or adsorbent resins may be selected for use in drawing certain air samples. For example, multiple air samples may be taken using different resins in order to detect the presence of different suspected airborne contaminants.

In the above description of the known use of the PUF cartridge, it is noted that opening 14 of the PUF cartridge 10 is uncovered and exposed to the atmosphere where it is desired to take an air sample. Thus, when vacuum is drawn so as to draw air through the PUF cartridge body, the air that passes through the PUF cartridge will necessarily be the air that immediately surrounds the PUF cartridge opening 14; that is the air sample will be air that is proximate to and surrounds the PUF cartridge. However, it has now been identified that there are instances when it is desired to take samples of air that are remote from the PUF cartridge body.

In the airline industry for example, it is sometimes desirable to take air samples from locations such as air vents. It may also be desired to take multiple air samples at different location points within the interior of a passenger airliner. Thus, for ease of working and taking samples, it is preferred to have a work station at which the operator operates a vacuum pump and collects PUF cartridge samples. However, the point at which the air will be sampled is distant from the work station. Thus, known methods of sampling air through a PUF cartridge cannot be accomplished without further modification and adaptation. In this embodiment, sample lines or wands will be pointed at those locations where it is desired to sample air.

Referring now to FIG. 2 there is shown a schematic view of a low volume PUF sampler adapter according to one embodiment of the present invention. Adapter 20 takes the general form of a cap that is fitted to cover the opening of a PUF cartridge. Adapter 20 is configured so as to define an interior 21 and an exterior 22.

Interior 21 of adapter 20 is generally hollow and conforms to the shape of the opening 14 of PUF cartridge 10. As the PUF cartridge is typically in the shape of a cylinder, the interior 21 of adapter 20 is also preferably cylindrical in shape. In a preferred embodiment, interior 21 of adapter 20 includes sealing surface 23 adapted so as to fit against the PUF cartridge exterior. Preferably the sealing surface comprises a washer or gasket 24 fitted in a groove 25 machined in the wall of interior 21.

Adapter further comprises a stop 26. In a preferred embodiment stop comprises a surface on the interior 21 of adapter 20. The stop acts as a limit of the travel that adapter 20 passes over opening 14 of PUF cartridge.

As also shown in FIG. 2 adapter 20 preferably comprises an aperture 27. In a preferred embodiment aperture 27 is centered on a surface of the exterior 22 of adapter 20. Aperture 27 is an opening that provides fluid communication through the adapter 20. When for example adapter 20 is affixed to a PUF cartridge, aperture 20 allows air to pass from the exterior 22 of the adapter 20 through aperture 27, through adapter 20, and into the interior 11 of the PUF cartridge 10. Preferably aperture 27 is positioned so that when adapter 20 is fitted over PUF cartridge 10, aperture 27 is centered over opening 14 of PUF cartridge.

Aperture 27 may be adapted for receiving fittings of various designs. In a preferred embodiment aperture includes threads for receiving a screw fitting. Alternatively aperture 27 may be sized for receiving tubing. A fitting is shown on aperture 27 in FIG. 3.

The sizing of adapter 20 may be adjusted to fit any desired PUF cartridge. PUF cartridges presently manufactured are approximately one inch in diameter at opening 14. Thus a preferred embodiment of adapter 20 has an interior diameter of approximately one inch.

In operation, adapter 20 is placed over opening 14 of a selected PUF cartridge. Adapter 20 is so placed, as by manual pushing, over the PUF cartridge, until the surface of PUF cartridge at the opening 14 contacts the limit of its travel at the adapter stop 26. FIG. 3 illustrates adapter 20 so placed onto PUF cartridge 10. The sealing surface 23 of adapter 20 fits securely against the exterior 16 of PUF cartridge 10. The fit between sealing surface 23 of adapter 20 and the exterior 16 of PUF cartridge is sufficiently secure so as to significantly prevent air passing to the interior of PUF cartridge across adapter sealing surface 23 when a vacuum is activated. While it is recognized that sealing surface 23 will not absolutely prevent air from passing across sealing surface 23, nevertheless, the secure seal will be sufficient when the air passing through PUF cartridge is substantially from that drawn through aperture 27 of adapter 20 rather than air across sealing surface 23. The seal at this point is a substantially airtight seal as explained below.

At various points in the description a seal or joint between system components is described as an airtight seal or a substantially airtight seal. Such a seal is not meant to be absolutely airtight so that no air whatsoever will pass through the seal when the system is in operation. Rather an airtight seal or substantially airtight seal means such a degree of seal that air contamination through the seal does not affect the analytical testing of the air sample in the system in any statistically significant way. Any leakage of air through a substantially airtight seal does not affect analysis of the air sample.

Referring now to FIG. 4 there is shown a schematic view of the low pressure adapter used in a sampling system. In operation a sample tubing 35 or sample line with two ends is further affixed to aperture 27 of adapter 20. Preferably, sample tubing 35 is affixed to a fitting that is itself affixed to aperture 27. The fixed end of tubing is the end affixed to adapter 20, and the opposite end of tubing is the free end. The sample tubing free end is then led to a sample point 50, a point where it is desired to take a sample of air, for example proximate to an air inlet vent of an aircraft interior. The sample tubing 35 is a hollow tubing of a dimension sufficient to pass air from the sample point to the aperture 27 of adapter 20. Further sample tubing 35 is of sufficient dimension to draw an adequate air sample for use with PUF cartridge 10.

The PUF cartridge has been previously loaded with a selected foam 12 and adsorbent resin 13. Exit 15 of the PUF cartridge is itself attached to a vacuum source, preferably vacuum pump 40. Additional tubing 30 preferably connects to a flow rate controlled vacuum pump source 40 (such as a pump) and PUF cartridge 10. At this point the system is ready to take an air sample. The vacuum is activated whereby tubing 30 transfers the vacuum to PUF cartridge 10 where a vacuum is induced within the interior 11 of the PUF cartridge. Air is thereby drawn at the sample point 50, through sample tubing 35, through the fitting, through aperture 27, through adapter 20, and through the PUF cartridge. In passing through the PUF cartridge the air sample reacts with the adsorbent resin 13. The vacuum is run for a sufficient time to draw a desired volume of air through the PUF cartridge and is then discontinued.

The configuration of the adapter covered PUF cartridge ensures that the air sample that passes through the PUF cartridge is substantially the air immediately surrounding the sample point and not the air at the PUF cartridge opening.

In accordance with proper air handling techniques, at this point the adsorbent resin 13 can be extracted from the PUF cartridge 10 and isolated so as to prevent further exposure to air. If desired the adsorbent resin 13 can then be analyzed for the presence of impurities including semivolatile compounds.

The adapter disclosed herein is particularly suited to methods of sampling air from the interior of an airplane fuselage. In many commercial airliner configurations, air may be introduced to the passenger area of the interior through multiple vents. The source of the air at these vents can itself be drawn from differing positions such as one of several engines, air from an engine bleed valve, an auxiliary power unit, ram air, or ambient air surrounding the airplane. Thus, in order to isolate the source of a suspected air impurity encountered in an airplane interior, it may be necessary to simultaneously sample air at several sample points from the airplane interior.

Figure 5:
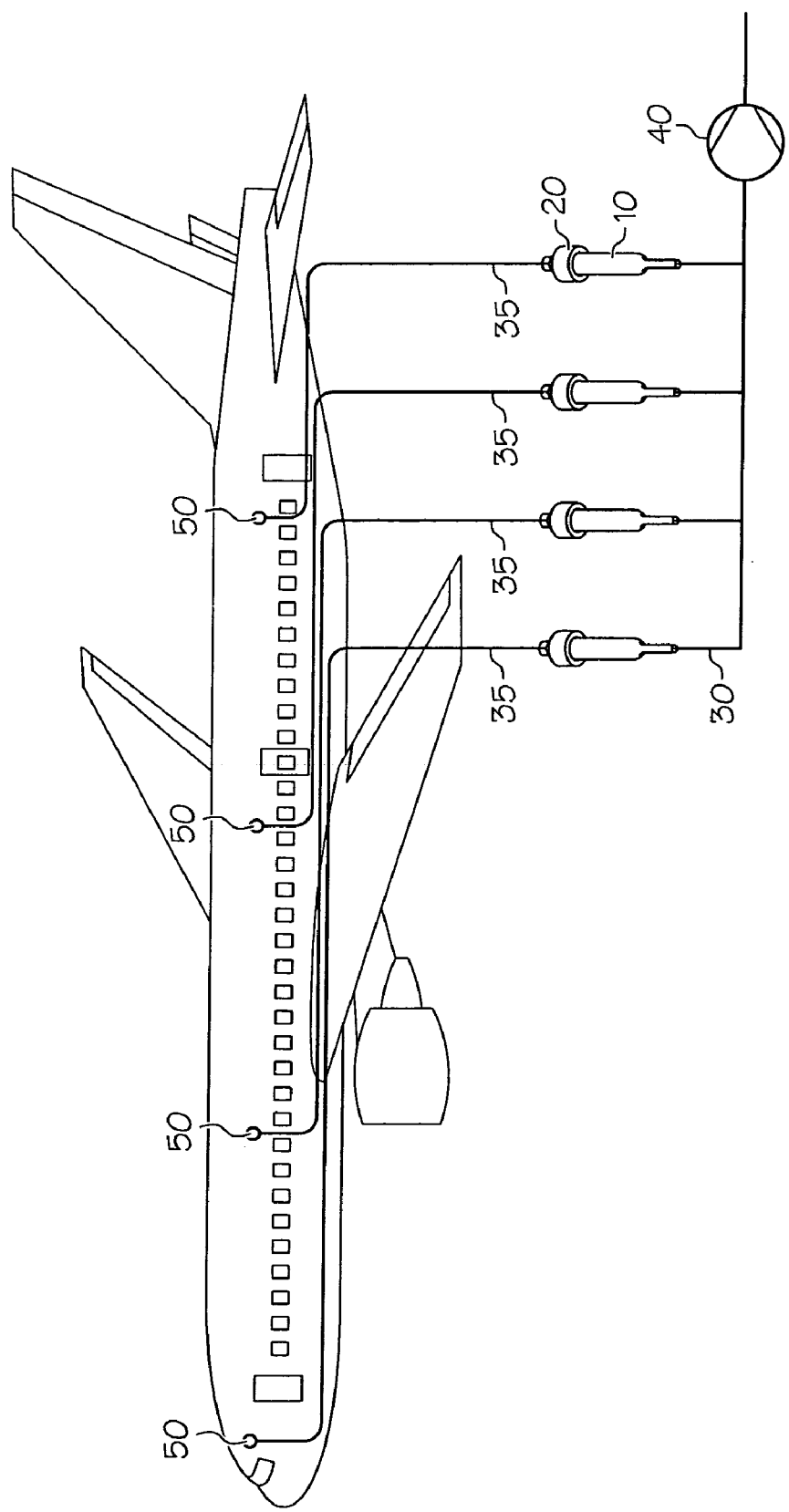
FIG. 5 is an illustration of a method of using the PUF sampler adapter in a multiple use configuration in accordance with an embodiment of the invention.

As shown in FIG. 5 multiple adapters 20 may be affixed to a number of PUF cartridges. For various reasons it may be desirable to simultaneously sample air from multiple sample points within an airplane. The present invention is adaptable to this purpose. The sample tubing 35 attached to each adapter 20 leads to a different sample point 50 within the aircraft. The exit 15 of each PUF cartridge may itself be attached to a flow rate controlled vacuum source 40 so that operation of the vacuum pump simultaneously or sequentially draws an air sample at each separate sample point 50. The sample points 50 may be spaced apart or otherwise isolated from each other so that air at each sample point 50 is substantially free of air at other sample points. Further, in this configuration the sample tubing preferably leads to a work station or collection point where each of the PUF cartridges 10 is located.

In this way an operator can first position the free end of the sample tubing 35 at desired target locations within the aircraft. The operator can then go to a working point, where the PUF cartridges 10 are located and rig each adapter and PUF cartridge combination. The operator can then operate the flow rate controlled vacuum. When finished, the operator can then gather each PUF cartridge and even repeat the sampling procedure if it is desired to obtain multiple samples for a given location.

It is frequently the case that air samples for testing purposes are drawn from an airplane while the plane rests in a hangar on the ground. Thus for operational convenience, the PUF cartridges may be positioned at a point in the plane exterior, such as a mobile testing bench, while the sample tubing that is affixed to the adapters is set at desired sample points within the aircraft. This allows for a more convenient and more efficient testing method of the aircraft interior.

While the invention has been described with reference to a preferred embodiment or embodiments, those skilled in the art will understand that various changes may be made and equivalents may be substituted for elements thereof without departing from the scope of the invention. In addition, many modifications may be made to adapt to a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for taking an air sample from a sample location, the apparatus comprising:
   a cylindrical PUF cartridge having an inlet opening, an exit opening, an interior region that defines a passage between the inlet and exit openings, and an adsorbent resin disposed within the passage, the inlet and exit openings each having a cross-sectional flow area, the inlet opening cross-sectional flow area greater than the exit opening cross-sectional flow area;

an adapter coupled to the PUF cartridge, the adapter including a body having a first section, a second section, and an interior surface defining a cavity, the body first section surrounding the cartridge inlet opening and having an opening formed therein that is in communication with the cavity, the body second section having an aperture formed therein that is in communication with the cavity, the aperture having a diameter that is smaller than the diameter of the opening;

a seal located on the body interior surface;

a vacuum source in fluid communication with the adapter aperture;

tubing coupled between the vacuum source and the PUF cartridge; and sample tubing coupled between the sample location and the adapter.

2. The apparatus according to claim 1 wherein the adapter sealingly engages with the PUF cartridge.

3. The apparatus according to claim 1, wherein the adapter interior surface includes a groove formed therein and further comprises a washer positioned within the groove and configured to seal against an exterior of the PUF cartridge.

4. The apparatus according to claim 1 wherein the adapter further comprises a stop.

5. The apparatus according to claim 1, wherein the adapter further comprises a fitting coupled to the adapter second section, the fitting having an end configured for receiving the sample tubing.

6. An apparatus for sampling air from a first and a second sample location, the apparatus comprising:

a first PUF cartridge having an inlet opening, an exit opening, an interior region that defines a passage between the inlet and exit openings, and an adsorbent resin disposed within the passage, the inlet and exit opening each having a cross-sectional flow area, the inlet opening cross-sectional flow area greater than the exit opening cross-sectional flow area;

a second PUF cartridge having an inlet opening, an exit opening, an interior region that defines a passage between the inlet and exit opening, and an adsorbent resin disposed within the passage, the inlet and exit openings each having a cross-sectional flow area, the inlet opening cross-sectional flow area greater than the exit opening cross-sectional flow area;

a first adapter coupled to the first PUF cartridge, the first adapter including a body having a first section, a second section, and an interior surface defining a cavity, the body first section surrounding the first PUF cartridge inlet opening and having an opening formed therein that is in communication with the cavity, the body second section having an aperture formed therein that is in communication with the cavity, the aperture having a diameter that is smaller than the diameter of the opening;

a first seal located on the first adapter body interior surface;

a second adapter coupled to the second PUF cartridge, the second adapter including a body having a first section, a second section, and an interior surface defining cavity, the body first section surrounding the second PUF cartridge inlet opening and having an opening formed therein that is in communication with the cavity, the body second section having an aperture formed therein that is in communication with the cavity, the aperture having a diameter that is smaller than the diameter of the opening;

a second seal located on the second adapter body interior surface;

a flow rate controlled vacuum source in fluid communication with the first and the second adapter apertures;

a first tubing coupled between the vacuum source and the first PUF cartridge;

a second tubing coupled between the vacuum source and the second PUF cartridge;

a first sample tubing having a first end positioned at the first sample location and a second end coupled to the first adapter;

a second sample tubing having a first end positioned at the second sample location, which is remote from the first sample location, and a second end coupled to the second adapter.

7. The apparatus according to claim 6 further comprising a first fitting positioned within the first adapter aperture and configured to receive the first sample tubing second end; and a second fitting positioned within the second adapter aperture and configured to receive the second tubing second end.

* * * * *